(12) United States Patent
Li et al.

(10) Patent No.: US 6,355,481 B1
(45) Date of Patent: Mar. 12, 2002

(54) HYBRIDOMA CELL LINE AND MONOCLONAL ANTIBODY FOR HUNTINGTIN PROTEIN

(75) Inventors: Xiao-Jiang Li; Shi-Hua Li, both of Tucker, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/596,938

(22) Filed: Jun. 19, 2000

Related U.S. Application Data

(60) Provisional application No. 60/140,018, filed on Jun. 18, 1999.

(51) Int. Cl.⁷ .................................................. C12N 5/20
(52) U.S. Cl. ..................... 435/331; 530/388.1; 435/326
(58) Field of Search .............................. 530/338.1, 300; 435/346, 4, 321, 326, 331

(56) References Cited

U.S. PATENT DOCUMENTS

| | | |
|---|---|---|
| 5,686,288 A | 11/1997 | MacDonald et al. |
| 5,693,757 A | 12/1997 | MacDonald et al. |
| 5,723,301 A | 3/1998 | Burke et al. |

OTHER PUBLICATIONS

Gutekunst et al., "Nuclear and Nueropil Aggregates in Huntington's Disease: Relationship to Neuropathology," *J. Neurosci.*, Apr. 1, 1998, pp. 2522–2534, vol. 19 (7).

Li et al., "Aggregation of N–Terminal Huntingtin is Dependent on the Length of Its Glutamine Repeats," *Human Molecular Genetics*, 1998, pp. 777–782, vol. 7, No. 5.

Sathasivam et al., "Formation of Polyglutamine Inclusions in Non–CNS Tissue," *Human Molecular Genetics*, 1999, pp. 813–822, vol. 8, No. 5.

Dorsman et al., "Analysis of the Subcellular Localization of Huntingtin with a Set of Rabbit Polyclonal Antibodies in Cultured Mammalian Cells of Neuronal Origin: Comparison with the Distribution of Huntingtin in Huntington's Diease Autopsy Brain", *Phil. Trans. R. Soc. Lond. B* (Jun. 1999) vol. 354, No. 1386, pp. 1061–1067.

Li et al., "Cellular Defects and Altered Gene Expression in PC12 Cells Stably Expressing Mutant Huntingtin," *J. Neurosci.*, (Jul. 1, 1999), vol. 19, No. 13, pp. 5159–5172.

Hazeki et al., "Rapid Aggregate Formation of the Huntingtin N–Terminal Fragment Carrying an Expanded Polyglutamine Tract," *Biochemical and Biophysical Reasearch Communications* (1999), vol. 256, pp. 361–366.

Lunkes et al., "A Cellular Model thast Recapitulates Major Pathogenic Steps of Huntington's Diease," *Human Molecular Genetics* (1998), vol. 7, No. 9, pp. 1355–1361.

Saudou et al., "Huntingtin Acts in the Nucleus to Induce Appotosis but Death Does Not Correlate with the Formation of Intranuclear Inclusions," *Cell* (Oct. 2, 1998), vol. 95, pp. 55–66.

Scherzinger et al., "Huntingtin–Encoded Polyglutamine Expansions Form Amyloid–like Protein Aggregates In Vitro and In Vivo," *Cell* (Aug. 8, 1997), vol. 90, pp. 549–558.

Sittler et al., "SH3GL3 Associates with the Huntingtin Exon 1 Protein and Promotes the Formation of Polygln–Containing Protein Aggregates," *Molecular Cell* (Oct. 1998), vol. 2, pp. 427–436.

Wilkinson et al., "Monoclonal Antibodies from Three New Regions of Huntingtin, the Huntington's Diease Protein," *Biochemical Society Transcations* (1997), vol. 25, p. 51S.

*Primary Examiner*—Lorraine Spector
*Assistant Examiner*—Dong Jiang
(74) *Attorney, Agent, or Firm*—Alston & Bird LLP

(57) ABSTRACT

The invention provides compositions and methods for the study, diagnosis, and treatment of Huntington's disease. Compositions comprise stably transfected cell lines that serve as a cellular model for Huntington's disease, sequences corresponding to an antigen associated with Huntington's disease, and monoclonal antibodies that bind specifically to said antigen. The stably transfected cell lines of the invention express truncated mutant huntingtin protein and display cellular defects similar to those observed in cells of patients with Huntington's disease. A method is provided wherein these cell lines are used to screen for therapeutic agents for the treatment of Huntington's disease. The monoclonal antibodies of the invention find use in a diagnostic assay for Huntington's disease.

4 Claims, 3 Drawing Sheets

HYBRIDOMA CELL LINE AND MONOCLONAL ANTIBODY FOR HUNTINGTIN PROTEIN

CROSS-REFERENCE TO RELATED APPLICATIONS

This application claims the benefit of U.S. Provisional Application Ser. No. 60/140,018 filed Jun. 18, 1999, which is hereby incorporated herein in its entirety by reference.

FIELD OF THE INVENTION

The invention relates to compositions and methods for the diagnosis and treatment of Huntington's disease. More specifically, the invention provides a cell line that stably expresses truncated mutant huntingtin protein for use as a model for Huntington's disease, antigens and monoclonal antibodies to mutant huntingtin protein, and methods for their use.

BACKGROUND OF THE INVENTION

Huntington's disease (HD) is a progressive neurodegenerative disorder characterized by motor disturbance, cognitive loss and psychiatric manifestations (Martin and Gusella (1986), N. Engl. J. Med. 315:1267–1276. It is inherited in an autosomal dominant fashion, and affects about 1/10,000 individuals in most populations of European origin (Harper, P. S. et al., in *Huntington's Disease*, W. B. Saunders, Philadelphia, 1991). The hallmark of HD is a distinctive choreic movement disorder that typically has a subtle, insidious onset in the fourth to fifth decade of life and gradually worsens over a course of 10 to 20 years until death. Occasionally, HD is expressed in juveniles typically manifesting with more severe symptoms including rigidity and a more rapid course. Juvenile onset of HD is associated with a preponderance of paternal transmission of the disease allele. The neuropathology of HD also displays a distinctive pattern, with selective loss of neurons that is most severe in the caudate and putamen regions of the brain. The biochemical basis for neuronal death in HD has not yet been fully explained, and there is consequently no treatment effective in delaying or preventing the onset and progression of this devastating disorder.

The molecular basis of HD is the expansion of a CAG repeat encoding a polyglutamine tract in the N-terminus of the HD protein huntingtin (Huntington's Disease Collaborative Research Group (1993) *Cell* 72:971–983). The length of the polyglutamine repeat is inversely correlated with the age of disease onset. A breakthrough in HD research was the development of transgenic mouse models for the disease. Transgenic mice expressing exon-1 of the human HD gene with an expanded CAG repeat develop a progressive neurological disorder that exhibits many of the features of HD, including choreiform-like movements, involuntary stereotypic movements, tremor, and epileptic seizures (Mangiarini et al. 1996 *Cell* 87:493–506). These mice have CAG repeats lengths of 141–157 while the huntingtin protein of normal mice contains 35 or fewer CAG repeats. Expansion of a CAG or glutamine repeat is associated with seven other inherited neurological disorders (MacDonald et al. (1996) *Curr. Opin. Neurobiol.* 6:638–643; Reddy and et al. (1997) *Curr. Opin. Cell. Biol.* 9:364–372; Ross (1997) *Neuron* 19:1147–1150).

Normally, huntingtin is a cytoplasmic protein characterized by high levels of expression in the striatal neurons vulnerable to degeneration in HD and low or undetectable expression levels in neurons resistant to degeneration (Ferrante et al. (1997), *Science* 227:770–773). Increasing evidence has shown that the expansion of the glutamine repeat in the huntingtin protein causes small protein fragments to accumulate and aggregate in the nucleus of cells. For instance, transgenic mice (Bates mice) expressing exon-1 of the HD gene containing >115 CAGs have neuronal intranuclear inclusions before they develop neurological disorders (Davies et al., (1997) *Cell* 90:537–548). Moreover, intranuclear aggregates containing N-terminal huntingtin fragments have been observed in the brains of HD patients (DiFiglia et al., (1997) *Science* 277:1990–1993); Becher et al., (1998) *Neurobiol. Dis.* 4:387–397; Gutekunst et al., (1999) *J. Neurosci.* 19:2522–2534).

The association between HD and nuclear aggregates has led to the hypothesis that such nuclear aggregates are toxic and play a causative role in the pathology of HD. In fact, several studies using cultured cells have shown that nuclear aggregates of polyglutamine proteins are associated with cell death (Cooper et al. (1998) *Hum. Mol. Genet.* 7:783–790); Martindale et al. (1998) *Nat. Genet.* 18:150–154; Hackam et al. (1999) *Hum. Mol. Genet.* 8:25–33; Moulder et al. (1999) *J. Neurosci.* 19:705–715). However, other studies show that the nuclear localization of polyglutamine proteins, not the formation of aggregates, is critical for neuronal pathology in transgenic mice (Klement et al. (1998) *Cell* 95:41–53) and in cultured striatal neurons (Saudou et al. (1998) *Cell* 95:55–66). In addition, the regional distribution of intranuclear aggregates in HD brains does not correspond to the neuropathology (DiFiglia et al., 1997; Becher et al., 1998; Gutekunst et al., 1999).

Despite the controversy surrounding the role of huntingtin aggregates in the pathology of HD, it is clear that expanded polyglutamine causes huntingtin to accumulate in the nucleus. Because many transcription factors contain a glutamine-rich domain and this domain can regulate their activity (Courey et al. (1988) *Cell* 55:887–898; Courey et al. (1989) *Cell* 59:827–836 ; Gerber et al. (1994) *Science* 263:808–811), it has been proposed that expanded polyglutamine-containing proteins interfere with gene transcription when they are localized to the nucleus. This possibility also provides a common mechanism to explain the features that HD shares with other glutamine-repeat diseases, including spinobulbar muscular atrophy and the spinocerebellar ataxias.

A HD cell model would be a useful tool in elucidating the mechanistic basis of HD. Most of the reported cell models have used transient transfection in which the expression levels of transfected protein vary greatly and influence aggregation of the transfected protein and cell viability. A stably transfected cell line that expresses mutant huntingtin is needed to provide a suitable approach to study whether intranuclear huntingtin affects cellular function at the transcription level, as well as other questions concerning the molecular basis of HD. Such a cell line would also allow for the establishment of a biochemical assay yielding consistent and reproducible results, which would greatly facilitate the screening and evaluation of potential HD therapeutic agents.

SUMMARY OF THE INVENTION

The present invention provides methods and compositions for the study, diagnosis, and treatment of Huntington's disease. Compositions comprise stably transfected cell lines, an antigen associated with Huntington's disease, and monoclonal antibodies specific for said antigen. The invention provides neuronal cell lines for use as a cellular model of Huntington's disease. More specifically, the invention provides rat pheochromocytoma PC12 cell lines that stably express truncated mutant huntingtin protein containing an expanded polyglutamine repeat. By "express" is intended that the cell line synthesizes the truncated mutant huntingtin protein, including the steps of transcribing, translating, and assembling truncated mutant huntingtin. These cell lines display the cellular defects observed in cells of patients with Huntington's disease. The PC12 cell lines of the invention can be maintained in culture for an extended period as continuous stable cell lines. The cells retain the morphological characteristics of the primary cells from which they were derived and the phenotypic traits associated with cells derived from animal models of Huntington's disease and Huntington's disease patients.

The methods and compositions of the invention find use in the study of the pathological mechanism of the mutant huntingtin in Huntington's disease and the development of therapeutic strategies for this disease.

In another embodiment of the invention, the methods and compositions are used in a screening assay to discover and evaluate therapeutic molecules for the treatment of Huntington's disease. The PC12 cell lines of the invention provide predictive in vitro test results of the effectiveness of therapeutic molecules, and can be used in a high through-out drug screening assay prior to screening of potential therapeutic molecules using animal models of the disease. This cell model reduces the cost and increases the efficiency of screening for such therapeutic molecules.

In another embodiment, monoclonal antibodies of the invention are used in a diagnostic assay for Huntington's disease. By "diagnostic assay" is intended an assay designed to distinguish one disease, in this case Huntington's disease, from other diseases with a similar clinical presentation. The monoclonal antibodies of the invention are without cross-reactivity to other proteins containing polyglutamine repeats, and react strongly with mutant huntingtin but weakly with wild-type rodent huntingtin. The diagnostic assay for Huntington's disease of the invention uses pre- or post-mortem tissue from an individual as a sample, and utilizes the Huntington's disease antigen and antibodies of the invention. The samples from the patient include, in addition to brain tissue, other tissues and cells including skeletal muscle, skin, heart, liver, adrenal glands, pancreas, kidney, stomach wall, duodenum, and mucosal cells.

DETAILED DESCRIPTION OF THE INVENTION

The present invention provides methods and compositions for the study, diagnosis, and treatment of Huntington's disease (HD). Compositions include transfected neuronal cell lines for use as cellular models of HD, monoclonal antibodies that bind to the to the HD gene product (huntingtin protein), and immunogenic polypeptides for the production of antibodies that selectively bind to mutant huntingtin protein. The methods and compositions of the invention find use in the study of the pathological mechanism of Huntington's disease and the development of therapeutic strategies and agents for this disease.

More specifically, the invention provides rat pheochromocytoma PC12 cell lines that stably express truncated mutant huntingtin protein containing expanded polyglutamine repeats. The cell lines of the invention display cellular defects similar to those observed in the cells of patients with HD and thus function as a cellular model for the disease.

The HD model cell lines of the invention are constructed by stably transfecting PC12 cells with an expression cassette comprising a nucleotide sequence encoding a truncated mutant huntingtin protein. The expression cassette additionally comprises an operably linked promoter which drives the expression of the truncated mutant huntingtin protein. By "truncated mutant huntingtin protein" or "truncated mutant huntingtin" is intended a polypeptide encoded by exon-1 of the human HD gene (GenBank Accession No. L27350) which encodes an N-terminal region of human huntingtin protein, wherein the nucleotide sequence encoding the polypeptide contains or is modified to contain a region coding for an expanded polyglutamine region. By "mutant huntingtin" or "mutant huntingtin protein" as used herein is intended a huntingtin protein (for example the human huntingtin protein of SwissProt Accession No. P42858) or any fragment of a huntingtin protein that contains an expanded polyglutamine region. By "expanded polyglutamine region" is intended a region of repeated glutamines wherein there are at least about 35 glutamines. The repeat region may comprise from about 35 or greater to up to 200 or greater glutamines. For purposes of the invention, any number of glutamines may be utilized as long as the region is greater than the length of the region found in normal huntingtin protein. Typically, the region comprises a 50, 75, 80, 100, 125, 150, or greater amino acid repeat. To isolate the PC12 cell lines expressing truncated mutant huntingtin protein, the transfected PC12 cells are serially subcloned until a cell line containing a homogenous population of transfected cells was established.

Figures 1A, 1B, 1C, 1D, 1E, 1F:
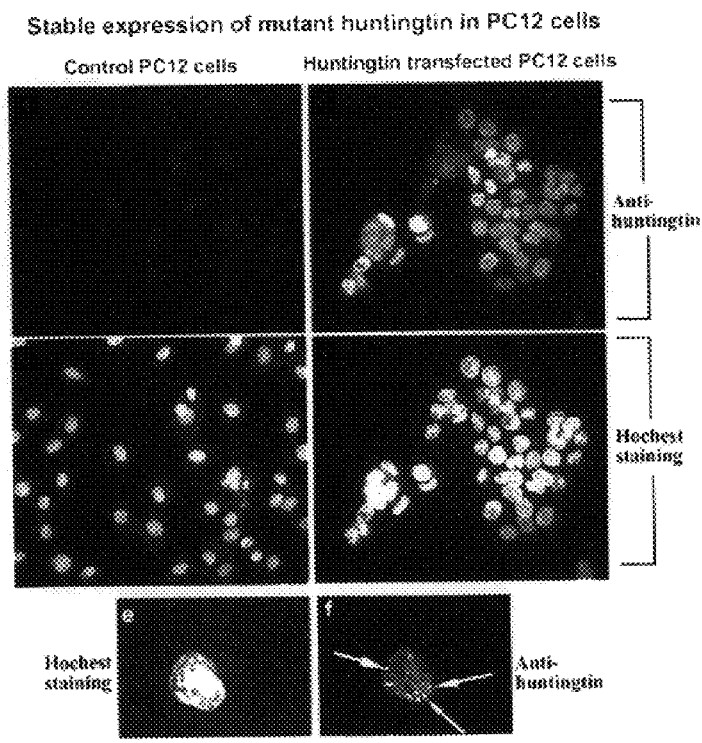
FIGS. 1A–1F. PC12 cells stably expressing the N-terminal fragment of huntingtin with 150 glutamine repeats. A and B are control PC12 cells transfected with pCDNA3 vector alone. C and D are PC12 cells transfected with a pcDNA3 construct containing huntingtin exon 1 plus 150 glutamines in the repeat. A and C show immunofluorescent staining of cells with the anti-huntingtin antibody. B and D show Hoechst staining of the nuclei of the cultured cells. Note that the transfected truncated mutant huntingtin is localized in the nuclei of stably transfected cells. These images were photographed at 400×. E and F show 1000× images of the nucleus of stably transfected cells. E shows Hoechst staining and F shows antibody labeling of the nucleus showing huntingtin aggregates (arrows) in the nucleus.
Figure 2:
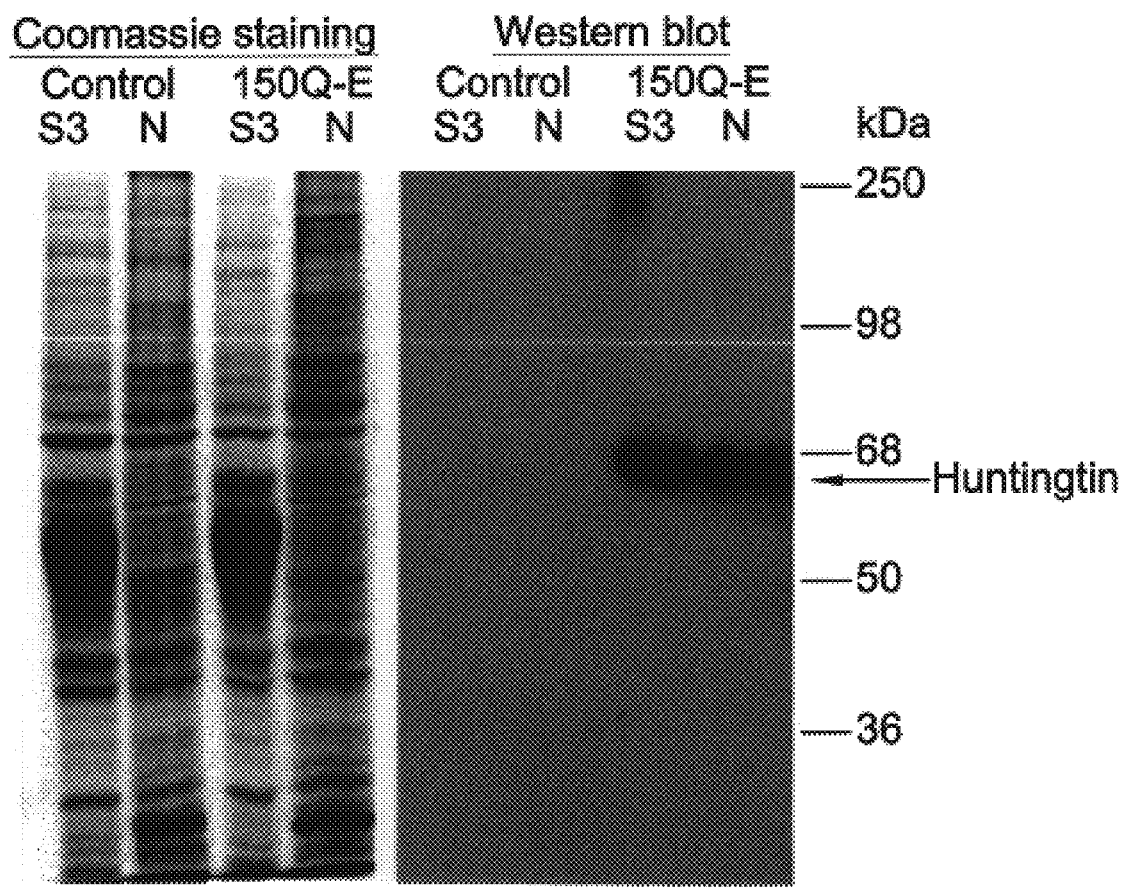
FIG. 2. Analysis of the distribution of mutant huntingtin in stably transfected PC12 cells by immunoblotting. PC12 cells stably expressing huntingtin exon 1 with 150 glutamines (150Q–E) were used for preparation of cytosolic (S3) and nuclear (N) fractions. These fractions were resolved by SDS-Page and detected by Coomassie blue staining and Western blotting with anti-huntingtin antibody. The control is PC12 cells transfected with pcDNA3 vector.
Figures 3A, 3B, 3C, 3D, 3E, 3F, 3G, 3H:
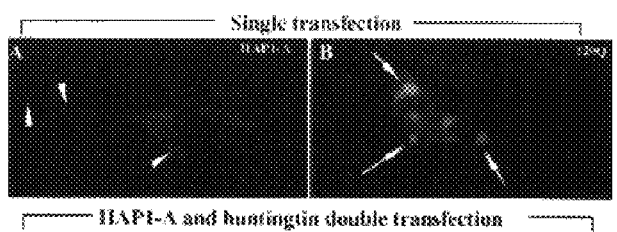
FIGS. 3A–3H. Cellular Localization of transfected truncated mutant huntingtin proteins with various glutamine-repeat lengths (HD-23Q, HD-73Q, HD-120Q) determined by immunofluorescence with anti-huntingtin monoclonal antibody. Cells were transfected with HAP 1-A (Huntington Associated Protein 1-A, A), or HD-120Q (B) alone. (C–H) Double transfection of HAP1-A and truncated mutant huntingtin with various glutamine repeat lengths [HD-23Q (C and D), HD-73Q (E and F), and HD-120Q (G and H)]. Transfected cells were stained with antibodies to HAP1-A (A, C, E, and G) or the monoclonal anti-huntingtin antibody described herein (B, D, F, and H). Arrowhead indicate HAP1-A puncta, whereas arrows indicate perinuclear inclusions formed by transfected huntingtin. These perinuclear inclusions are also labeled by anti-HAP1-A antibody, suggesting that they contain transfected HAP1-A. Because the overexpressed proteins produced very strong staining, the immunofluorescent exposure was adjusted to reveal only transfected.

As a non-limiting example, a cell line that is stably transfected with a truncated mutant huntingtin protein containing a 150 amino acid repeat (150Q) is described in Example 1 of the Experimental section. As shown in FIG. 1 and FIG. 2, the expression and nuclear localization of truncated mutant huntingtin 150Q protein in the 150Q cell line was verified by immunofluorescent staining and immunoblotting with E48, a polyclonal antibody that preferentially binds to aggregates of mutant huntingtin protein.

An isolated nucleic molecule encoding a mutant huntingtin protein will comprise a region of CAG repeats. As noted for the protein, the length of the CAG repeats may vary, so long as the number of CAGs is greater than the number of CAGs in the normal gene. Thus the length of the CAG trinucleotide repeat may vary from about 35 copies and greater up to at least 200 copies and greater, preferably about 50 copies, about 75 copies, about 100 copies, about 125 copies, about 150 copies or greater. The term "huntingtin" or "huntingtin protein" refers to a huntingtin protein (for example, the protein sequence of Swiss Prot Accession no. P42858) that is encoded by the Huntington disease gene (for example the gene given in GenBank Accession No. Ac005516), or a fragment or variant of such a protein. Fragments include peptides comprising amino acid sequences sufficiently identical to or derived from the amino acid sequence of huntingtin, and exhibiting at least one activity of a huntingtin, but which includes fewer amino acids than the full-length huntingtin protein. Variants of a huntingtin protein generally retain the functional activity of huntingtin protein. Variants include polypeptides that differ in amino acid sequence due to natural allelic variation or mutagenesis.

The transformed cell lines of the invention display the phenotypic characteristics required of an HD cellular model and thus can be used as a model to study the disease and to screen for pharmaceutical therapies for the disease. These characteristics are (1) the accumulation of mutant huntingtin protein in the cell nucleus, and (2) expression of the neuronal dysfunction and cellular defects observed for the cells of patients with HD. The majority of the expressed truncated mutant huntingtin protein in the transformed cells was in the nucleus of the cells and these cells display multiple cellular defects including abnormal morphology, high death rate, hypersensitivity to apoptotic stimulation, and defective neurite development (described in Example 1). In the example, it is shown that these defects are correlated with the expression level of the mutant 150Q huntingtin protein. The transformed PC12 cell lines of the invention can be maintained in culture for an extended period and passaged more than 50 times without losing their HD-like properties. The cells retain the morphological characteristics of the primary cells from which they were derived and the phenotypic traits associated with cells derived from animal models of Huntington's disease and Huntington's disease patients. The transformed cell lines of the invention may be passaged for multiple generations, including greater than 50 generations, or more, without loss of phenotype.

The effects of the presence of intranuclear mutant huntingtin on cell function and morphology observed for the transformed cell lines of the invention are described in Example 1. These effects include increased cell-cell adhesion after prolonged culturing, non-uniform cell shape including flattened or polygonal cells and increased cell diameter, shortened cellular processes and fewer cells with processes, a reduction in neurite growth in response to neurotrophic factors, decreased cell viability, and an increased sensitivity to apoptotic stimulation.

The scope of this invention includes, in addition to the transformed PC12 cell line Q150, other rat pheochromocytoma PC12 cell lines that are stably transfected with an expression cassette comprising a sequence encoding a truncated mutant huntingtin. These cell lines are produced by the methods described above and in Example 1, which include the steps of transfecting cells with a cDNA encoding a truncated mutant huntingtin protein, subcloning the cells such that each cell line contains a homogenous population of transfected cells (i.e. a population of cells with similar morphological characteristics that express similar amounts of mutant huntingtin protein), and verifying that the cell lines retain the HD phenotypic characteristics for greater than 50 generations.

One embodiment of this invention is the use of the cell lines of the invention to study the molecular mechanistic basis of HD in order to develop therapeutic strategies for treatment of this disease. Example 2 and Example 3 of this application describe two such uses. Example 2 details the use of the 150Q cell line to investigate the effect of intranuclear mutant huntingtin protein on neurite outgrowth and Example 3 describes the use of the same cell line to demonstrate that intranuclear mutant huntingtin can alter gene expression.

Another aspect of the present invention is the use of the cell lines of the invention in an assay to enable screening, including high throughput screening, of potential therapeutic agents for HD. Such a biochemical assays yield consistent and reproducible results and are less expensive and time intensive than are animals models of the disease.

In one embodiment of the screening assay, a truncated mutant huntingtin expressing PC12 cell line of the invention is contacted with a test molecule or agent and the accumulation of huntingtin protein in the nucleus of these cells is monitored to determine the efficacy of the test molecule. In another embodiment, the ability of the test molecule to reduce the effects of the mutant huntingtin protein on cellular function or morphology is determined. These effects on cellular function or morphology are described above and in Examples 1–3 and include increased cell-cell adhesion after prolonged culturing, non-uniform cell shape including flattened or polygonal cells and increased cell diameter, shortened cellular processes and fewer cells with processes, a reduction in neurite growth in response to neurotrophic factors, increased cell death, and an increased sensitivity to apoptotic stimulation.

The test compounds or agents of the screening assay can be obtained using any of the numerous approaches in combinatorial library methods known in the art, including biological libraries, synthetic library methods requiring deconvolution, the "one-bead one-compound" library method, solid phase or solution phase libraries, and synthetic library methods using affinity chromatography selection. The biological library approach is limited to peptide libraries, while the other four approaches are applicable to small molecule, peptide, or nonpeptide oligomer libraries of compounds (Lam (1997) *Anticancer Drug Des.* 12:145).

Methods for the synthesis of molecular libraries can be found in the art, for example in: DeWitt et al. (1993) *Proc.*

Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), plasmids (Cull et al. (1992) Proc. Natl. Acad. Sci. USA 89:1865–1869), spores (U.S. Pat. Nos. 5,571,698; 5,403, 484; and 5,223,409), or phage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

In another embodiment, the truncated mutant huntingtin expressing PC12 cell lines of the invention are used in an assay to determine the potential therapeutic efficacy of a therapeutic agent for HD before testing the agent in an animal model of the disease. By "therapeutic efficacy" is intended the capacity of an agent to produce a desired therapeutic effect. In the present invention, the desired therapeutic effect is the treatment of HD, i.e. the reduction or elimination of the symptoms of HD, and/or a halt or decrease in the rate of progression of the disease, and/or a reduction of the deleterious effects on cellular growth and function.

In another embodiment, the cell lines of the present invention are used in an assay to monitor the effectiveness of treatment of an individual, such as an individual in a clinical trial, with a therapeutic agent for HD disease.

As another aspect, the present invention encompasses an anti-huntingtin monoclonal antibody that specifically bind huntingtin protein without cross-reactivity to other proteins containing polyglutamine repeats. The antibodies of the invention react strongly with mutant human huntingtin but weakly with wild-type rodent huntingtin.

The invention also encompasses nucleotide sequences and amino acid sequences (for example the amino acid sequence SEQ ID NO:1) corresponding to an antigen useful for raising antibodies that bind selectively to mutant huntingtin protein. This property is referred to herein as the antigen's "antigenic activity." The huntingtin antigen of SEQ ID NO:1 corresponds to amino acids 1–256 of human huntingtin protein (SwissProt Accession No. P42858), modified such that the polyglutamine region is reduced to two glutamines and the polyproline region is reduced to four polyprolines. The present invention also encompasses fragments and variants of the amino acid sequence of SEQ ID NO:1. Fragments of the amino acid sequence of SEQ ID NO:1 of the a include peptides comprising amino acid sequences sufficiently identical to or derived from the amino acid sequence of SEQ ID NO:1, and exhibiting the activity (including but not limited to the antigenic activity) of the amino acid sequence given in SEQ ID NO:1, but which include fewer amino acids than the full-length amino acid sequence of SEQ ID NO:1. Variants of the amino acid sequence of SEQ ID:1 generally retain the activity (including but not limited to the antigenic activity) of the sequence. Variants include polypeptides that differ in amino acid sequence from SEQ ID NO:1 due to natural allelic variation or mutagenesis.

The present invention also encompasses sequences that are sufficiently identical to the amino acid sequence of SEQ ID NO:1, fragments and variants of the amino acid sequence of SEQ ID NO:1, and nucleotide sequences encoding the amino acid sequence of SEQ ID NO:1 and fragments and variants thereof. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

The percentage of identity between two sequences can be determined using a mathematical algorithm. A nonlimiting example of a mathematical algorithm utilized for the comparison of two sequences is the algorithm of Karlin and Altschul (1990) Proc. Natl. Acad. Sci. USA 87:2264, modified as in Karlin and Altschul (1993) Proc. Natl. Acad. Sci. USA 90:5873–5877. This algorithm is incorporated into the NBLAST and XBLAST programs of Altschul et al. (1990) J. Mol. Biol. 215:403. BLAST nucleotide searches can be performed with the NBLAST program, score=100, wordlength=12, to obtain nucleotide sequences similar to the nucleic acid molecules of the invention. BLAST protein searches can be performed with the XBLAST program, score=50, wordlength=3, to obtain amino acid sequences similar to protein molecules of the invention. To obtain gapped alignments for comparison purposes, Gapped BLAST can be utilized as described in Altschul et al. (1997) Nucleic Acids Res. 25:3389. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) CABIOS 4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

A hybridoma cell line expressing one monoclonal antibody of the invention was deposited with American Type Culture Collection (ATCC), 10801 University Boulevard, Manassas, Va., on June 28, 2000, and assigned Patent Deposit Number PTA-2179. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The present invention provides assays for detecting huntingtin protein in the context of a biological sample. The term "biological sample" is intended to include tissues, cells, and biological fluids isolated from a subject, as well as tissues, cells, and fluids present within a subject. The anti-huntingtin monoclonal antibody can be used to detect huntingtin protein (e.g., in a cellular lysate or cell supernatant) and determine its abundance and expression pattern. As an additional example, anti-huntingtin antibodies can be used to diagnose the disease or to monitor huntingtin levels in tissue as part of a clinical testing procedure, for example, to determine the efficacy of a given treatment regimen.

The diagnostic assay provided herein for Huntington's disease uses pre- or post-mortem tissue from an individual as a sample, and utilizes the Huntington's disease immunogenic peptide and antibodies of the invention. The samples to be assayed for huntingtin expression include, in addition to brain tissue, other tissues and cells including skeletal muscle, skin, heart, liver, adrenal glands, pancreas, kidney, stomach wall, duodenum, and mucosal cells (see Sathasivam et al. (1999) *Hum. Mol. Genetics* 8:813–322). The sample used in the assay of the invention is preferably selected from the group consisting of brain tissue, pre or post-mortem, cerebrospinal fluid, urine and blood.

In one embodiment, the presence or absence of huntingtin proteins in a biological sample (e.g. a skeletal muscle sample from a patient or a post-mortem tissue sample from brain) is assayed by obtaining a biological sample from a test subject and contacting the biological sample with the anti-huntingtin monoclonal antibody of the invention such that the presence of huntingtin protein can be detected in the biological sample. Results obtained with a biological sample from the test subject may be compared to results obtained with a biological sample from a control subject.

The anti-huntingtin monoclonal antibody can be labeled to facilitate huntingtin protein detection in the biological sample. The term "labeled", with regard to the antibody, encompasses both direct labeling of the probe or antibody by coupling (i.e., physically linking) a detectable substance to the probe or antibody, as well as indirect labeling of the probe or antibody by reactivity with another reagent that is directly labeled. Methods of indirect labeling include detection of the anti-huntingtin monoclonal antibody by using a labeled secondary antibody.

Detection of huntingtin protein can also be facilitated by coupling the anti-huntingtin monoclonal antibody, or a secondary antibody that bind the anti-huntingtin monoclonal antibody, to a detectable substance. Detectable substances include, but are not limited to, various enzymes (for example, horseradish peroxidase, alkaline phosphatase, β-galactosidase, or acetylcholinesterase), prosthetic groups (for example, streptavidin/biotin or avidin/biotin), fluorescent materials (for example, umbelliferone, fluorescein, fluorescein isothiocyanate, rhodamine, dichlorotriazinylamine fluorescein, dansyl chloride or phycoerythrin), luminescent materials (for example, luminol), bioluminescent materials (for example, luciferase, luciferin, and aequorin), and radioactive materials (for example, $^{125}I$, $^{131}I$, $^{35}S$, or $^3H$).

In one embodiment of the diagnostic assay of the invention, a fluorescently labeled anti-huntingtin monoclonal antibody or secondary antibody is used, and the levels and cellular localization of the huntingtin protein in the biological sample are determined using any immunohistochemical techniques known in the art, for example the techniques described herein.

Other methods for determining the presence of antigen specific to Huntington's disease in a sample are also provided, for example, the biological sample can be contacted with a first anti-huntingtin antibody specific for a first antigenic determinant of huntingtin such that a first antibody-antigen complex is formed; separating the first complex from the sample; contacting the first complex with at least one second antibody specific for a second antigenic determinant on the huntingtin protein, where the second antigenic determinant may be the same as said first antigenic determinant. The second antibody binds to the first complex to produce a second complex which can be detected by the antibody labeling techniques described above. The levels of the second complex correlate with the presence of antigen specific to Huntington's disease in the sample.

In the diagnostic assay described above, the first antibody can be attached to a suitable solid matrix, for example polystyrene beads. The sample is then contacted with an effective amount of the first antibody to produce a first complex. The contact preferably involves adding the sample to a column of polystyrene beads coated with the first antibody. This complex first antibody is isolated from the sample by any of the elution methods known to those skilled in the art. The isolated first complex is contacted with at least one second antibody as described above.

The presence of the labeled antibody bound to the huntingtin antigen of the complex consisting of antigen bound to the first and second antibody may be readily detected using well-known techniques. For example, if the detectable antibody is linked to an enzyme conjugated to an appropriate substrate, the optical density of the detectable bound antibody may be determined using a spectrophotometer. If the detectable antibody is fluorescently labeled, the fluorescent emission may be measured using a fluorometer. In a similar manner, if the detectable antibody is radioactively labeled, the bound antibody may be detected using a techniques known in the art, including scintillation counting and autoradiography. By comparing the results obtained using the above-described methods on the test sample with those obtained using the methods on a control sample, the presence of the antigen specific to Huntington's disease may be determined. The elevated amount of antigen specific to Huntington's disease is thereby detected and may optionally be quantitated. In this method, the first and second antibody may be monoclonal antibodies, or the first or the second detectable antibody can be a polyclonal antibody.

The anti-huntingtin monoclonal antibodies of the invention may be used in a therapeutic composition for the treatment of HD. The association between HD and nuclear aggregates has led to the idea that such nuclear aggregates are toxic and play a causative role in the pathology of HD. In fact, several studies using cultured cells have shown that nuclear aggregates of polyglutamine proteins are associated with cell death (Cooper et al (1998) *Hum. Mol. Genet.* 7:783–790; Martindale et al. (1998) *Nat. Genet.* 18:150–154; Hackman et al. (1998) *Hum. Mol. Genet.* 8:25–33; Moulder et al. (1999) *J. Neurosci.* 19:705–715). Evidence also suggests that the level of aggregation of mutant huntingtin protein is determined by the length of the polyglutamine regions in the amino terminus of the protein (Martindale et al. (1998) *Nat. Genet.* 18:150–154). As a non-limiting example of a mechanism for the efficacy of the anti-huntingtin monoclonal antibody of the invention in the treatment of HD, the anti-huntingtin monoclonal antibody binds to its epitope in the amino terminus of the mutant huntingtin protein, immediately proximal to the glutamine repeat region, and thereby disrupts the formation of toxic mutant huntingtin aggregates.

The antibodies of the invention may similarly be used to modulate (i.e. upregulate or downregulate) the activity of huntingtin protein, including mutant huntingtin protein. Any activity or process mediated by huntingtin protein can be modulated, for example, cell-cell adhesion properties, number and/or length of processes on cells, rate of neurite outgrowth in response to neurotrophic factors, level of cell death, and sensitivity to apoptotic stimulation.

The anti-huntingtin monoclonal antibodies (also referred to herein as "active compounds") of the invention can be incorporated into pharmaceutical compositions suitable for administration. Such compositions typically comprise the antibody and a pharmaceutically acceptable carrier. By "pharmaceutically acceptable carrier" is intended to include solvents, dispersion media, coatings, antibacterial and antifungal agents, isotonic and absorption delaying agents, which are suitable for pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The anti-huntingtin monoclonal antibody is provided in therapeutically effective amounts. By "therapeutically effective amount" is intended an amount sufficient to modulate the symptoms associated with huntingtin. The therapeutically effective amount may vary depending on age, sex, weight, symptoms, and other factors. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the anti-huntingtin monoclonal antibody can include a single treatment or, preferably, can include a series of treatments. It will also be appreciated that the therapeutically effective amount of the antibody may increase or decrease over the course of treatment. Changes in dosage may result and become apparent from the results of diagnostic assays as described herein.

The invention is illustrated further by the following examples which are not to be construed as limiting.

EXPERIMENTAL

Example 1
Production of a Cellular Model for Huntington's Disease

A stably transfected rat pheochromocytoma PC12 cell line that expresses a protein corresponding to human HD exon-1 with an expanded polyglutamine region consisting of a 150 amino acid repeat (150Q) was established. Examination by electron microscopy showed that the majority of transfected truncated mutant huntingtin is diffuse in the nucleus. These cells have defective morphology and decreased viability. Compared with control PC12 cells, cells expressing 150Q have altered expression of multiple genes. The results described below indicate that intranuclear truncated mutant huntingtin may alter gene expression and induce various cellular defects.

Material and Methods

Antibodies and reagents. Glutathione S-transferase (GST) fusion protein antibody, EM48, that is specific to the N-terminal region (amino acids 1–256) of human huntingtin has been described previously (Li et al. (1998) *Hum. Molec. Genet.* 7:777–782; Gutekunst et al. (1999) *J. Neurosci.* 19:2522–2534). Mouse monoclonal antibody to tubulin (E7) was purchased from the Developmental Studies Hybridoma Bank (Iowa City, Iowa). Anti-p75$^{NTR}$ (antibody 9992) was provided by Dr. Moses V. Chao (New York University Medical Center). Anti-TrkA/ nerve growth factor (/NGF) was provided by Dr. Louis Reichardt (University of California, San Francisco). Anti-huntingtin-associated protein (-HAP1) was made in our previous studies (Li et al., (1995) *Nature* 378:398–402). NGF (2.5 S), epidermal growth factor (EGF), cell culture media, and newborn calf serum were obtained from Life Technologies (Gaithersburg, Md.). Other reagents used in this study were staurosporine (Sigma, St. Louis, Mo.), ciliary neurotrophic factor (CNTF; Promega, Madison, Wis.), horse serum (Hyclone, Logan, Utah), and Hoechst 33258 (Molecular Probes, Eugenc, Oreg.). G418 was obtained from Life Technologies.

Cell cultures. Dr. James J. Lah in the Department of Neurology at Emory University (Atlanta, Ga.) provided rat pheochromocytoma PC12 cells (Lah et al. (1993) *J. Neurochem.* 60:503–512). PC12 cells were grown in DMEM supplemented with 5% fetal bovine serum and 10% horse serum, containing 100 µg/ml penicillin and 100 µg/ml streptomycin, and were incubated at 37° C. in a humidified 5% $CO_2$ atmosphere. Cells were grown in dishes or chamber slides (Nunc, Naperville, Ill.) at densities ranging from 2 to $4 \times 10^4$ cells/$cm^2$. The culture media were changed every 48–72 hr.

Huntingtin constructs, transfection, and selection of stably transfected cell lines. A partial huntingtin CDNA containing 20 (20Q) or 150 CAG repeats was isolated from a lambda phage DNA that contains exon-1 of the human HD gene [provided by Dr. Gillian Bates (Mangiarini et al. (1996) *Cell* 87:493–506)]. The N-terminal huntingtin fragments encoded by these cDNAs were expressed using the pCIS expression vector that carries a cytomegalovirus promoter (Li et al. (1998) *Hum. Molec. Genet.* 7:777–782). The pCDNA3 vector, which carries the G418 resistance gene (Invitrogen, San Diego, Calif.), was cotransfected with the pCIS-huntingtin constructs. Subconfluent PC12 cells in 80 mm dishes were transfected with 7 µg of plasmid DNA and 10 µg/ml lipofectAMINE (Life Technologies) per dish. The transfected cells were then selected in the presence of 500 µg/ml G418 in DM EM plus 5% fetal bovine serum and 10% horse serum. Selected G418-resistant cells were subcloned and maintained in the same conditioned medium until each cell line contained homogenous transfected cells. The expression of transfected huntingtin in PC12 cells was verified by immunofluorescent staining with EM48. After 3–4 months of selection and subcloning, three cell lines expressing 150Q and five cell lines expressing 20Q were obtained. 150Q-9 and 20Q-1 cells have been passaged for >50 generations without apparent loss of phenotypes. Cultures were maintained at 37° C. in a 5% $CO_2$ incubator, with the medium changed every 48–72 hr. The experiments described here were performed with cloned cells of generation numbers 20–50.

Immunoblot analysis. Cultured cells were collected and solubilized in SDS sample buffer. Protein samples were then resolved by 10 or 12% SDS-PAGE. Blots were incubated with EM48 (1:1000), and immuno-reactive bands were visualized using a chemiluminescence kit (Amersham, Arlington Heights, Ill.). EM48 immunoreactivity could be eliminated by overnight preabsorption of the antibody with 20 µg/ml GST-huntingtin but not GST alone. Protein expression levels were assessed by quantification of the intensities of the protein bands on the blots using a Personal Densitometer S1 (Molecular Dynamics, Sunnyvale, Calif.).

Immunofluorescent labeling of cultured cells. Transfected cells grown in chamber slides were fixed in 4% paraformaldehyde in PBS for 15 min, permeabilized with 0.4% Triton X-100 in PBS for 30 min, blocked with 5% normal goat serum (NGS) in PBS for 1 hr, and incubated with primary antibodies in 2% NGS and PBS overnight at 4° C. After several washes, the cells were incubated with secondary antibodies conjugated with either FITC or rhodamine (Jackson ImmunoResearch, West Grove, Pa.). Hoechst dye (1 μg/ml) was used to label the nuclei. A Zeiss fluorescent microscope (Axioskop 2) and video system (Dage-MTI, Michigan City, Ind.) were used to capture images. The captured images were stored and processed using Adobe Photoshop software.

Electron microscopy. Electron microscopic immunocytochemistry was performed on transfected cells using methods described previously (Li el al., (1997) *Neurosci. Lett.* 223:153–156). Briefly, transfected cells were fixed in 4% (w/v) paraformaldehyde and 0.2% glutaraldehyde in 0.1 M phosphate buffer (PB), pH 7.2, for 30 min, permeabilized in 0.05% Triton X-100 in PBS for 30 min, and preincubated with 5% NGS in PBS for 1 hr. For immunogold labeling, the cells were incubated with primary antibody EM48 (1:1000) and then treated with 1.4 nm gold-conjugated Fab fragments of goat anti-rabbit IgG (Nanoprobes, Stony Brook, N.Y.) at 1:50 in Tris-buffered saline (TBS), pH 7.2, containing 2% NGS, silver-enhanced using the IntenSEM kit (Amersham International, Buckinghamshire, England), osmicated (1% $OsO_4$ PB), dehydrated, and embedded in Eponate. Ultrathin sections (60–70 nm) were cut using a Leica Ultracut S ultramicrotome, (Nussloch, Germany). Thin sections were counterstained with 5% aqueous uranyl acetate for 5 min followed by Reynolds lead citrate for 5 min and were examined using a Hitachi H-7500 electron microscope.

For better preservation of the morphology of cells, we fixed some transfected cells with 3% glutaraldehyde in PB. Ultrathin sections (60–70 nm) of these cells were used for electron microscopic examination without immunogold labeling.

Cell death rate and neurite outgrowth assays. Cells were plated at a standard density ($4 \times 10^4/cm^2$) in six-well plates with DMEM supplemented with 5% FBS and 10% horse serum. Cultured cells were harvested, centrifuged at 1000 rpm for 5 min, and resuspended in PBS containing 0.4% trypan blue. The cells were incubated in the trypan blue solution for 10 min and transferred to a hemocytometer, and the number of viable (phase bright) and nonviable (blue) cells was recorded. For each sample, cell counts in four corner fields of the hemocytometer were averaged.

To evaluate neurite outgrowth, we plated the cells at low density ($2 \times 10^4$ Cells/cm$^2$) onto six-well plates. Cell cultures were treated with NGF (100 ng/ml) for 48 hr or with staurosporine (50–100 nM) and EGF (10 ng/ml) for 16 hr and were fixed with 4% paraformaldehyde in PBS for 15 min. After several washes with PBS, cells with neurites exceeding the cell diameter were counted using an inverted microscope (Olympus Optical CK2, Tokyo, Japan). At the same time, five to seven images (10×) were captured by a Pixera camera, and the percentage of cells with neurites was confirmed by analyzing these images. On average, 500–800 cells were counted for each group.

Cell viability and apoptosis assays. Cell viability was determined by a modified 3-(4,5-dimethylthiazol-2-yl)-2,5-diphenyltetrazohum bromide (MTS) assay (Cell Titer 96; Promega), which is based on the conversion of tetrazolium salt 3-(4,5-dimethylthiazol-2-yl)-5-(3-carboxymethoxyphenyl)-2-(4-sulfophenyl) 2-H-tetrazolium by mitochondrial dehydrogenase to a formazan product, as measured at an absorbance of 490 nm. PC12 cells were plated in 96-well plates at a density of 10,000 cells/well and maintained 16–24 hr in complete medium. Cells were then changed to medium containing 1% FBS in the absence or presence of staurosporine at different concentrations. Staurosporine was dissolved in 2 mM dimethylsulfoxide (DMSO) and diluted in the medium at various concentrations. Leptomycin B (LMB; 10 nM) [provided by Dr. Minoru Yoshida (Kudo et al. (1997) *J. Biol. Chem.* 272:29742–29751)] was added to the medium for 12–16 hr. After drug treatment, 20 μl of MTS reagent (2.1 mg/ml) was added to each well. The cells were then incubated for 30–45 min at 37° C. in a 5% $CO_2$ incubator. The reaction was stopped by adding 25 μl of 10% SDS. The plates were read with a microplate reader (SPECTRAmax Plus; Molecular Devices, Palo Alto, Calif.) at 490 nm. Each data point was obtained using a triplet-well assay.

Apoptosis was measured using a terminal deoxynucleotidyl transferase-mediated biotin-dUTP nick end labeling (TUNEL) assay kit (Promega). Briefly, cells were grown in six-well plates ($2 \times 10^5$ cells/well) in complete medium. After 48 hr of culture, cells were collected and centrifuged at 1000×g for 5 min. Cells were resuspended in PBS with 0.1% BSA at $1 \times 10^6$ cells/ml. Twenty microliters of the cells mixed with 200 μl of PBS and 0.1% BSA were spun onto a glass slip using a cytospincentrifuge (Shadon Lipshaw, Pittsburgh, Pa.). Cells were fixed with 4% paraformaldehyde in PBS for 15 min, permeabilized with 0.2% Triton X-100 in PBS for 15 min, and then incubated with fluorescent-labeled nucleotide in the presence of terminal deoxynucleotidyl transferase. The cells were then examined using a Zeiss fluorescent microscope (Axioskop 2) and video system. The percentage of apoptotic cells was obtained by counting 600–2000 cells for each group.

Gene expression studies. Wild-type PC12, 20Q-1, and 150Q-9 cells were used for examining their gene expression. Differential display PCR was performed using the GenHunt RNAimage kit (Nashville, Tenn.) and following the manufacturer's instructions. Reverse transcription (RT)-PCR and Northern blot analysis were performed as described previously (Li et al., (1998) *J. Biol. Chem.* 273:19220–19227). Primers for RT-PCR were acgaccccttcattgacctc (sense; SEQ ID NO.:2) and gggggctaagcagttggtgg (antisense; SEQ ID NO.:3) for glyceraldehyde-3-phosphate dehydrogenase (GAPDH) (Tso et al., 1985), tgtggaagtgggggatgacg (sense; SEQ ID NO:4) and gcactcagcaagaaagacct (antisense; SEQ ID NO:5) for TrkA/NGF (Meakin et al., 1992), ccacattc-cgacgactgatg (sense; SEQ ID NO:6) and ccaagaatgacgcactaac (antisense; SEQ ID NO:7) for another NGF receptor p75$^{NTR}$ (Radeke et al., (1987) *Nature* 325:593–597), ggagagcaggacggactttt (sense; SEQ ID NO:8) and ccagaggggtcatcaatcca (antisense; SEQ ID NO:9) for metallothionein-II (Andersen et al. (1986) *Mol. Cell. Biol.* 6:302–314), ggttttcattggagggttgc (sense; SEQ ID NO:10) and ctgtctgccacgggtttctc (antisense; SEQ ID NO:11) for the glutamate transporter GLAST (Tanaka (1993) *Neurosci. Lett.* 159:183–186), and cagcgttgtacgtcttatggg (sense; SEQ ID NO:12) and ggggattggtccaactgtgg (antisense; SEQ ID NO:13) for HAP1 (Li et al. (1995) *Nature* 378:398–402). First-strand cDNA was generated from RNA of cultured PC12 cells. PCR conditions were 95° C. for 45 sec, 60° C. for 1 min, and 72° C. for 2 min with 35 cycles. PCR products were electrophoresed on a 1% agarose gel.

For Northern blotting, nitrocellulose membranes containing equal amounts of total RNAs from control PC12 cells and transfected PC12 cells were hybridized with [$^{32}$P]dCTP-labeled PCR products obtained with primers as described above. The blots were hybridized in 50% formamide and 5×saline-sodium phosphate-EDTA hybridization buffer at 42° C. and washed with 0.2×SSC and 0 and 5% SDS at 55° C. before exposure to x-ray films.

Statistical analysis. All values were expressed as mean±SD. Statistical significance was assessed by ANOVA followed by Scheffe's test; p<0.05 was considered significant.

Results

Establishment of Stably Transfected PC12 Cells

An expanded polyglutamine (115–150 glutamines) has been shown to cause the HD exon-1 protein to form aggregates in the neuronal nucleus in Bates transgenic mice (Davies et al., 1997). Rat PC12 cells were chosen for transfection because this cell line is of neuronal origin and can grow neurites (Greene et al. (1976) Proc. Natl. Acad. Sci. USA 73:2424–2428). The cDNA of HD exon-1 with 150 CAG repeats was transfected into PC12 cells. The same DNA fragment with a normal CAG repeat (20Q) was also expressed in PC12 cells and served as a control. Using G418 (500 μg/ml) to select stably transfected PC12 cells, three independent clones (150Q-1, -5, and -9) that expressed the 150Q mutant HD exon-1 protein and five independent clones (20Q-1, -3, -4, -5, and -8) that expressed the 20Q HD exon-1 protein were obtained. The expression of transfected huntingtin in these cell lines was confirmed by Western blots using EM48, which recognizes the N-terminal region of huntingtin (Li and Li, 1998). 150Q migrated much slower than 20Q in the SDS gel because it contains an expanded polyglutamine that hinders protein migration (Aronin et al. (1995) Neuron 15:1193–1201). Expression levels of 150Q in the three 150Q cell lines appeared to be different, and there was also a slight difference in the migration of the transfected 150Qs in the gel. The difference in these bands may reflect a small variation in glutamine-repeat numbers, which could result from the instability of the very long CAG repeat in transfected cells.

To determine whether the transfected proteins were overexpressed in these cells, nuclear and cytosolic fractions were examined by Coomassie blue staining. Comparison of the protein profile of the extracts from stably transfected cells and parental PC12 cells did not reveal any additional bands at the same molecular weight as that of 20Q or 150Q. Thus, it is unlikely that the transfected proteins were expressed at a very high level in stably transfected cells. Because both 20Q and 150Q were expressed at a similar level, these cells were useful for examining cellular defects associated with polyglutamine expansion.

Abnormal morphology and intranuclear huntingtin localization. 20Q-1 and 150Q-5 lines were chosen for extensive characterization of transfected huntingtin in PC12 cells because they have intermediate expression levels. It was observed that the morphology of 150Q cells was different from that of 20Q and control PC12 cells. First, 150Q cells were more likely to clump together, especially when they had been growing for >36 hr, suggesting an increase in cell-cell adhesion after prolonged culturing. Second, the shapes of the 150Q cells were not uniform; some were round, but most appeared flattened or polygonal. Most round cells had a diameter of <15 μm, which was similar to that of parental PC12 and 20Q cells. However, flattened cells were often 20–30 μm in diameter. The appearance of different shapes is unlikely to be attributable to the possibility that the original isolate was not truly clonal; even repeated recloning of the roundest cells still produced the same cell. Instead, characterization of other transfected cell lines suggested that the cell growth stages and/or the expression of 150Q may contribute to these various sizes and shapes. Third, most parental PC12 and 20Q cells were round cells with short processes, generally no more than the diameter of the cell body. However, fewer 150Q cells had processes, and their processes were much shorter.

Because the expansion of polyglutamine causes huntingtin to localize in the nucleus and to form aggregates in transgenic mice (Davies et al. (1997) Cell 90:537–548; Ordway et al. (1997) Cell 91:753–763), the subcellular localization of transfected proteins was examined using EM48 immunofluorescence. It was found that the majority of the expressed 150Q was in the nucleus of PC12 cells. Very intense immunolabeling was seen in the nucleus, and weak labeling was observed in the cytoplasm of 150Q cells. The nuclear labeling was further confirmed by staining cells with the nuclear DNA dye Hoechst. Parental PC12 cells had very weak immunolabeling. Furthermore, 20Q cells displayed intense labeling in the cytoplasm and weak labeling in their nuclei, a pattern that is in striking contrast to that for 150Q cells. The contrasting distribution of 20Q and 150Q clearly indicates that expanded polyglutamine causes huntingtin to accumulate in the nucleus. Other cell lines were examined and it was found that all the 20Q cell lines had intense cytoplasmic EM48 staining whereas all the 150Q cell lines displayed intense intranuclear EM48 staining. This result confirmed that 20Q and 150Q are distributed differently in all transfected PC12 cell lines.

It is notable that not all transfected cells had the same intensity of EM48 immunolabeling, perhaps because their stage in the cell cycle influenced the expression level of the transfected protein. A striking finding is that the majority of 150Q was uniformly distributed in the nucleus and very few cells (<3%) had aggregates in their nuclei. On explanation for this is that the aggregation of huntingtin is time-dependent and that nuclear division during cell proliferation prevents the formation of aggregates.

Electron microscopic examination of 150Q cells. To confirm the nuclear localization of 150Q in PC12 cells, electron microscopic examination of ultrathin sections was performed using EM48 immunogold labeling. Most immunogold particles were evenly distributed in the nucleus in 150Q cells. Almost no immunogold particles were found in the nucleus of control 20Q cells. This result confirmed that 150Q is indeed enriched in the nucleus and that expanded polyglutamine does cause huntingtin to remain in the nucleus.

Aggregates could not be detected by immunogold labeling. Because the fixation for immunogold labeling might not preserve the ultrastructure of cultured cells, we performed electron microscopic examination, with a higher concentration (3%) of glutaraldehyde and no immunostaining, to identify any aggregates. Using this method, we observed aggregate-like structures in the nucleus of some cells. Less than 3% of the 150Q cells had these structures, suggesting that intranuclear aggregates, if any, are very uncommon in these cells. It has been reported that morphological changes within the nuclear membrane, such as indentation, follow the formation of nuclear aggregates in Bates transgenic mice (Davies et al. (1997) Cell 90:537–548). 150Q cells that were not dividing and had a single, intact nucleus were examined, but no notable difference in the nuclear membrane structure of 150Q cells as compared with that of 20Q and parental PC12 cells was observed.

The ultrastructure of other intracellular structures such as mitochondria, smooth and rough endoplasm reticulum, the Golgi complex, and the plasma membrane was also examined. The ultrastructure of all organelles and membranes appeared the same as that in parental PC12 or 20Q cells.

150Q cells lack the neurite extension response to nerve growth factor. A distinct neuronal property of PC12 cells is that they can differentiate and grow neurites in response to neurotrophic factors. Interestingly, 150Q cells were unable to develop normal neurite outgrowth even after treatment with 100 ng/ml NGF for 3 d. In contrast, most (75–85%) 20Q cells, like parental PC12 cells, had long neurites after the same NGF treatment. The subcellular distribution of transfected proteins in NGF-treated cells was also examined using the EM48 immunofluorescent-staining assay. The result showed that 20Q was expressed in the neuronal processes in differentiated cells, whereas 150Q was still concentrated in the nucleus. The lack of neurites on 150Q cells was unlikely to be attributable to G418 selection or heterogeneity of parental PC12 cells because all three independent cell lines of 150Q had the same defect in neurite outgrowth, whereas all five 20Q cell lines grew neurite as well as the controls. It was also unlikely that these 150Q cells had lost their neuronal properties because staurosporine, a drug that acts directly on intracellular signaling pathways, could still stimulate neurite extension of 150Q cells as described below.

The trophic effects of other growth factors, including interleukin-6 (IL-6; 20 ng/ml), CNTF (20 ng/ml), EGF (10 ng/ml), and basic fibroblast growth factor (bFGF; 20 ng/ml) were also examined. All of these factors act on plasma membrane receptors. CNTF did not promote neurite outgrowth in control PC12 cells. EGF had a very weak effect on neurite extension. IL-6 promoted neurite outgrowth of parental PC12 and 20Q cells, but it had a weaker effect than that of NGF and bFGF. However, all of these trophic factors failed to promote neurite outgrowth in 150Q cells. Thus, in 150Q cells, there might be an impairment of a number of membrane receptors or of intracellular signaling pathways.

Staurosporine induces neurite outgrowth of 1500 cells. Despite their lack of neurite response to NGF, 150Q cells were able to develop neurites in the presence of staurosporine. Staurosporine has been shown to induce neurite outgrowth by its regulation of gene expression (Tischler et al.(1990) *J. Neurochem.* 55:1159–1165; Tischler et al. (1991) *J. Biol. Chem.* 266:1141–1146; Gollapudi et al. (1997) *J. Neurosci. Res.* 49:461–474; Yao et al. (1997) *J. Biol. Chem.* 272:1821–18266). It also induces apoptosis of cultured cells by inhibiting protein kinases (Koh et al. (1995) *Exp. Neurol.* 135:153–159; Boix et al. (1997) *Neuropharm.* 36:811–821). To evaluate both neurite extension and cell death, we treated cells with staurosporine and used a trypan blue exclusion assay. Parental PC12 cells that had been treated with 100 nm staurosporine grew neurites without displaying significant cell death, an observation that is similar to that in a previous report (Yao et al. (1997) *J. Biol. Chem.* 272:18261–18266). However, this concentration of staurosporine killed a significant number of 150Q cells, although some of the living 150Q cells displayed neurite outgrowth. Because the effect of staurosporine on neurite outgrowth could be greatly enhanced by EGF (Raffioni and Bradshaw, 1995), we treated 150Q cells with EGF and staurosporine together. Interestingly, EGF significantly enhanced neurite outgrowth and reduced cell death.

150Q cells are susceptible to apoptotic stimulation. Because EGF increases the proliferation rather than the differentiation of PC12 cells (Huff et al. (1981) *J. Cell Biol.* 88:189–198), it was reasoned that EGF might enhance staurosporine-induced neurite outgrowth by increasing cell viability. To confirm the susceptibility of 150Q cells to staurosporine, the tetrazolium dye (MTS) assay was used to measure cell viability quantitatively. The 150Q cells were more susceptible to 10–125 nM staurosporine than were the 20Q or parental PC12 cells. Hoechst dye staining of the nuclei clearly revealed DNA fragmentation in dead 150Q cells. Higher doses (>250 nM) of staurosporine also killed more 20Q cells than parental PC12 cells, supporting the idea that normal N-terminal fragments of huntingtin could also be toxic if they are overexpressed (Hackam et al. (1998) *J. Cell Biol.* 141:1097–1105). Treating 150Q cells with EGF (10 ng/ml) significantly increased cell viability in the presence of 10–100 nM staurosporine. Thus, EGF does have a protective effect on staurosporine-induced cell death.

The expression levels of 150Q and cell death rate. If 150Q is associated with the cellular defects observed in the 150Q-5 line, the expression levels of 150Q should correlate with the extent of the cellular defects. Western blot results indicated that the three 150Q cell lines express different levels of huntingtin. To confirm this, the expression of 150Q was compared with that of dynactin P150$^{Glued}$ and native huntingtin using Western blotting and densitometry. The ratio of 150Q to dynactin P150$^{Glued}$ was used to reflect the relative expression level of 150Q. The expression of 150Q was lowest in the 150Q-1 line, intermediate in the 150Q-5 line, and highest in the 150Q-9 line.

To examine whether 150Q can cause spontaneous cell death, the viability of the three 150Q cell lines was measured in the absence of any apoptotic stimulation. Parental PC12 and 20Q cells served as controls. All 150Q cells displayed abnormal morphology; the 150Q-1 line had more small round cells than did the other two lines. In contrast, 150Q-9 cells were generally larger than 150Q-1 and 150Q-5 cells and were more likely to clump together. It is likely that varied expression levels of 150Q account for these differences. To assess the relationship between the expression of 1500 and cell death quantitatively, the same number of cells were plated. 150Q cell lines and control cell lines grew at similar proliferation rates. However, all 150Q cell lines had more dead cells than did control PC12 cells, and the number of dead cells differed for the three 150Q cell lines at various times during culturing. The 150Q-9 line had more dead cells than did the 150Q-5 line, which, in turn, had more than did the 150Q-1 line. Thus, the extent of cell death is correlated with the expression level of 150Q in transfected cells.

To confirm that spontaneous cell death is indeed mediated by an apoptotic mechanism, a TUNEL assay was used to examine apoptotic cells after 48 hr of culture. A significantly greater number of apoptotic cells was found in 150Q cells than in parental or 20Q cells. Quantitative assessment showed that 1.1% of PC12, 0.9% of 20Q, 6.4% of 150Q-1, 9.1% of 150Q-5, and 25.5% of 150Q-9 cells underwent apoptosis.

To confirm further that the cell viability is associated with the intranuclear level of 150Q, 150Q cells were treated with LMB, a drug that blocks nuclear export of RNA and a number of proteins by binding to the nuclear exporting protein CRM1 (Fornerod et al. (1997) *Cell* 90:1051–1060; Fukuda et al. (1997) *Nature* 390:308–311; Kudo et al. (1997) *J. Biol. Chem.* 272:29742–29751; Ossareh-Nazari et al. (1997) *Science* 278:141–144; Wolff et al. (1997) *Chem. Biol.* 4:139–147). After LMB treatment, more 150Q cells had intense intranuclear EM48 labeling than did those without LMB treatment. LMB also increased the nuclear labeling of some 20Q cells. This result suggests that the HD exon-1 protein may passively diffuse into the nucleus and be exported by LMB-sensitive proteins. How the expanded polyglutamine protein accumulates in the nucleus is unclear. More importantly, more 150Q cells showed DNA fragmentation after treatment with LMB. In contrast, very few LMB-treated 20Q cells had DNA fragmentation. This observation was validated by quantitative measurement of cell viability; more 150Q cells than control cells were dying after exposure to LMB. The increases in both nuclear 150Q staining and cell death by LMB suggest that intranuclear huntingtin is associated with cell death.

Discussion

One of the goals of these studies was to develop a cell line that models the nuclear accumulation of the truncated mutant huntingtin. This goal was achieved using PC12 cells transfected with the HD exon-1 protein with 150 glutamine repeats. An HD cellular model should have two features: (1) expanded polyglutamine causes huntingtin to accumulate in the nucleus, and (2) the expression of truncated mutant huntingtin is associated with neuronal dysfunction. The cell model of this invention has these features. First, polyglutamine expansion causes the HD exon-1 protein to accumulate uniformly in the nucleus of PC12 cells. Second, PC12 cells expressing expanded polyglutamine huntingtin display multiple cellular defects including abnormal morphology, high death rate, hypersensitivity to apoptotic stimulation, and defective neurite development. These defects appear to be correlated with the expression level of 150Q in different cell lines. Furthermore, this cell model also provides evidence of the idea that the intranuclear localization of huntingtin affects gene expression.

It is known that only N-terminal huntingtin fragments, which are generated by proteolytic cleavage of full-length huntingtin, are able to enter the nucleus and form aggregates (Hackam et al. (1998) *Hum. Mol. Genet.* 8:25–33; Li et al. (1998) *Hum. Mol. Genet.* 7:777–782; Martindale et al. (1998) *Nat. Genet.* 18:150–154). Polyglutamine expansion also causes other disease proteins to enter the nucleus and form aggregates in dentatorubral and pallidoluysian atrophy (Becher et al. (1998) *Neurobiol. Dis.* 4:387–397; Igarashi et al. (1998) *Nat. Genet.* 18:111–117), spinal and bulbar muscular atrophy (Li et al. (1998) *Ann. Neurol.* 44249–254), and several forms of spinocerebellar ataxia (Paulson et al. (1997) *Neuron* 19:333–344; Skinner et al. (1997) *Nature* 389:971–974; Holmberg et al. (1998) *Hum. Mol. Genet.* 7:913–918). However, the mechanisms for the nuclear translocation and retention of huntingtin may differ from those for other polyglutamine proteins. For instance, the spinocerebellar ataxia-1 (SCA1) protein ataxin-1 carries a consensus nuclear localization signal (NLS), and deletion of the NLS prevents ataxin-1 from entering the nucleus (Klement et al. (1998) *Cell* 95:41–53). Similarly, the SCA3 protein ataxin-3 also has an NLS, and its nuclear translocation does not require the presence of polyglutamine (Tait et al. (1998) *Hum. Mol. Genet.* 7:991–997). On the other hand, the HD exon-1 protein does not have an NLS; instead, the expansion of the glutamine repeat causes this protein to accumulate in the nucleus. Because fragments of N-terminal huntingtin enter the nucleus more easily, it has been proposed that intranuclear localization of mutant huntingtin may rely on passive diffusion (Hackam et al. (1998) *J. Cell. Biol.* 141:1097–1105). If so, the accumulation of huntingtin with expanded polyglutamine is likely caused by its increased association with nuclear molecules. This possibility is supported by the findings that polyglutamine expansion causes huntingtin to interact avidly with other specific proteins (Li et al. (1995) *Nature* 378:398–402; Trottier et al. (1995) *Nature* 378:403–406; Burke et al. (1996) *Nat. Med.* 2:347–350; Sittler et al., 1998). One of these proteins is GAPDH, which is also found to bind to other polyglutamine proteins (Burke et al. (1996) *Nat. Med.* 2:347–350; Koshy et al. (1996) *Hum. Mol. Genet.* 5:1311–1318) and to be translocated into the nucleus during apoptosis (Sawa et al. (1997) *Proc. Natl. Acad. Sci. USA* 94:11669–11674; Ishitani et al. (1998) *Mol. Pharmacol.* 53:701–707; Saunders et al. (1999) *J. Neurochem.* 72:925–932). It will be interesting to study whether the interaction between GAPDH and 150Q is involved in the nuclear localization of 150Q. It is also equally possible that 150Q binds more weakly to nuclear exporting proteins than does 20Q. This possibility is supported by our finding that LMB increased intranuclear huntingtin staining.

The EM study described above shows that most 150Q cells had a diffuse, nuclear distribution of huntingtin rather than the inclusions or aggregates that are seen in transgenic mice. A recent study showed that the peak appearance of intranuclear aggregates in cultured primary neurons occurs 6 d after huntingtin transfection (Saudou et al. (1998) *Cell* 95:55–66). However, PC12 cells divide every 2–3 d, which may not be long enough for 150Q to form aggregates. The aggregation of huntingtin may also depend on protein concentration. This may explain why transient transfection of cultured cells, which often results in protein overexpression, can produce huntingtin aggregates even in dividing cells (Cooper et al. (1998) *Hum. Mol. Genet.* 7:783–790; Li and Li (1998) *Hum. Molec. Genet.* 7:777–782; Martindale et al. (1998) *Nat. Genet.* 18:150–154). It is also possible that cells having huntingtin aggregates may not be able to survive during stable transfection. It has been reported that chaperone (Cummings et al. (1998) *Nat. Genet.* 19:148–154, proteasome (Chai et al. (1999) *Hum. Mol. Genet.* 8:673–682, and transglutaminase (Igarashi et al. (1998) *Nat. Genet.* 18: 111–117; Kahlem et al. (1998) *Mol. Cell.* 1:595–601) regulate aggregation of polyglutamine proteins. If G418 selection alters the activity of these cellular factors, it could also influence the aggregation of 150Q in the stably transfected cells. Nevertheless, the association between cellular defects and the diffuse nuclear localization of 150Q favors the idea that the nuclear localization of polyglutamine proteins is sufficient to induce cellular toxicity (Klement et al. (1998) *Cell* 95:41–53; Saudou et al. (1998) *Cell* 95:55–66).

Several cellular defects were observed in 150Q cells. These defects included increased cell death, susceptibility to the apoptotic agent staurosporine, abnormal morphology, and defective neurite development. Cell death could also be related to abnormal metabolism; this hypothesis is currently under investigation. The abnormal morphology and defective neurite development in 150Q cells are intriguing because the degeneration of neuronal processes also occurs in HD (Ferrante et al. (1985) *Science* 230:561–563; Graveland et al. (1985) *Science* 227: 770–773; Sotrel et al. (1993) *Neurology* 43:2088–2096. The observation has been made that, in early HD brains, neuropil aggregates precede the formation of intranuclear aggregates (DiFiglia et al. (1997) *Science* 277:1990–1993; Gutekunst et al. (1999) *J. Neurosci.* 19:2522–2534). The formation of neuropil aggregates in vivo could be associated with or accelerated by the degeneration of neuronal processes. The lack of normal neurite outgrowth in 150Q cells might reflect the dysfunction of molecules or proteins that are important for maintaining normal neuronal processes.

Example 2

Use of Cells Expressing Truncated Mutant Huntingtin to Investigate the Effect of this Protein on Neurite Outgrowth N-terminal fragments of mutant huntingtin protein have been reported to accumulate and form inclusions in the nucleus of the brain cells of HD patients. The effect of the intranuclear localization of truncated mutant huntingtin protein on neurite development was investigated in PC12 cells.

Results

To assess the relationship between neurites and the expression levels of 150Q, cells were treated with 100 nM staurosporine; this concentration of staurosporine induces significant neurite formation in PC12 cells. To prevent cell death, EGF (10 ng/ml) was used in combination with staurosporine so neurites of 150Q cells could be maintained.

Neurite development was evaluated by measuring the percentage of cells having one or more neurites that exceed one cell body diameter. After staurosporine and EGF treatment, most parental and 20Q cells had long neurites (3–4 cell body diameters). Some 150Q cells also displayed shorter neurite outgrowth (1–2 body diameters). However, the number of cells with neurites appeared to be different among the three 150Q cell lines. Quantitative analysis showed that 88.1% of parental PC12 cells and 92.2% of 20Q cells had neurites. In contrast, 31.2% of 150Q-1, 23.2% of 150Q-5, and 13.5% of 150Q-9 cells had neurites. Thus, the expression level of 150Q in these cells was inversely correlated with the number of cells forming neurites.

Staurosporine initiates neurite outgrowth in PC12 cells within a fairly short period of time (4–6 hr) by acting directly on intracellular signaling pathways (Yao et al. (1997) *J. Biol. Chem.* 272:18261–18266). If the initiation of neurite outgrowth by staurosporine is affected by the intranuclear huntingtin concentration, which varies among individual cells because of differences in the cell cycle, we might see that cells with neurites would have less 150Q in their nuclei than did cells without neurites. By performing EM48 immunofluorescent staining of 150Q cells treated with EGF and staurosporine, it was observed that most of the cells with neurites displayed much less EM48 labeling in their nuclei than did undifferentiated cells. Cells that clumped together and displayed larger body size often had intense intranuclear EM48 labeling. Approximately 87% of the cells with neurites displayed very weak EM48 staining within their nuclei, whereas only 31% of the cells without neurites had a similar weak immunolabeling. Immunofluorescent double labeling was also performed with EM48 and an antibody to a-tubulin. Cells containing tubulin-immunoreactive neurites often displayed weak and diffuse EM48 labeling. Some cells had both intense cytoplasmic and nuclear staining for EM48. However, in cells that did not have long neurites, EM48 immunolabeling was often intense in their nuclei. This observation further supports the idea that the presence of 150Q in the nucleus is associated with the abnormal morphology and lack of neurite growth in PC12 cells.

Discussion

The extent of cellular defects is correlated with the expression level of 150Q. The extent of neurite outgrowth induced by staurosporine is also inversely correlated with the expression levels of 150Q. It is possible that the cell biology of each individual cell line may not be identical and could also contribute to the variation in cellular defects. Transfection of cells using inducible expression could more accurately control the expression of transfected huntingtin and thus reveal in great detail the relationship between cellular defects and 150Q expression. The striking observation of the present study, however, is that cells expressing 150Q often have an intranuclear accumulation of huntingtin and display abnormal morphology and defective neurite outgrowth. On the other hand, 20Q cells in which huntingtin is mainly distributed in the cytoplasm do not show such abnormalities. Furthermore, inhibiting nuclear transport can significantly increase 20Q and 150Q in the nucleus but causes more 150Q cells than 20Q cells to die. These observations strongly support the idea that intranuclear mutant huntingtin plays a causative role in cellular defects.

Example 3
Use of PC12 Cells Stably Expressing Truncated Mutant Huntingtin Protein to Demonstrate that Intranuclear Mutant Huntingtin can Alter Gene Expression N-terminal fragments of mutant huntingtin protein have been reported to accumulate and form inclusions in the nucleus of the brain cells of HD patients. The truncated mutant huntingtin protein that is stably expressed in transfected PC12 cells is also localized to the nucleus. The nuclear localization of this mutant protein prompted the examination of its affect on gene expression, as the combined altered gene expression of a number of genes could result in cellular dysfunction.

Results 150Q-9 cells were chosen for the study because this cell line has the highest expression level of truncated mutant huntingtin and thus would be most likely to reveal an alteration in the expression of a particular gene. The 20Q cells served as a control to verify that the altered gene expression is associated with the expanded polyglutamine. To compare the expression of a subset of the total genes expressed in 20Q and 150Q cells, differential display PCR was used with a set of primers that are reportedly able to screen one-fifth of a cell's total transcripts. 35 PCR products were observed that showed an obvious difference in intensity; some were more intense in the 20Q samples, whereas some were more intense in the 150Q samples. The altered expression levels of some PCR products in 150Q cells were confirmed using reverse Northern blotting as suggested by the manufacturer. Thus, these PCR products might be derived from transcripts that have different levels in 20Q and 150Q cells.

The genes in 150Q cells that show different expression levels in the differential display PCR might not be readily identified by individual subcloning and sequencing. Because it was observed that 150Q cells had defective neurite outgrowth in response to NGF, the expression of $p75^{NTR}$, a subunit of the NGF receptor, was examined using RT-PCR with specific primers for $p75^{NTR}$. Primers for GAPDH were also included in the same PCR reaction to determine whether $p75^{NTR}$ expression is specifically altered in comparison with GAPDH. The result showed fewer $p75^{NTR}$ products in 150Q cells than in 20Q cells. To validate this result, Northern blot analysis was also performed. The result showed that transcripts for $p75^{NTR}$ were indeed reduced in 150Q cells compared with wild-type PC12 cells and 20Q cells. To determine whether the RT-PCR assay could detect altered expression of other genes, the expression of HAP1, a neuronal huntingtin-associated protein identified previously and thought to be involved in neuronal intracellular transport (Engelender et al. (1997) *Hum. Mol. Genet.* 6:2205–2212; Gutekunst et al. (1998) *J. Neurosci.* 18:7674–7686; Li et al. (1998) *J. Biol. Chem.* 273:19220–19227; Martin et al. (1999) *J. Comp. Neurol.* 403:421–430) was examined. Both RT-PCR and Northern blot analysis consistently showed a decreased expression of HAP1 in 150Q cells.

Because the NGF receptor consists of two peptides, $p75^{NTR}$ and TrkA/NGF (Chao (1992) *Neuron* 9:583–593;

Carter et al. (1997) *Neuron* 18:187–190), the expression of TrkA/NGF transcripts was also examined. TrkA/NGF expression was also found to be downregulated in 150Q cells. Because differential display PCR also suggests that some genes are upregulated in 150Q cells, RT-PCR was used to examine the expression of two known genes. These genes are metallothionein-II (MII), a cysteine-rich, heavy metal-binding protein that protects cells from oxidative damage (Karin (1985) *Cell* 41:9–10; Schwarz et al. (1995) *Proc. Natl. Aca. Sci. USA* 92:2252–4456), and the glutamate transporter (GLAST), a plasma membrane protein for glutamate uptake (Danbolt (1994) *Prog. Neurobiol* 44:377–396). In agreement with the previously reported differential display PCR results, MII was decreased and GLAST was increased in 150Q cells when compared with the control cells.

It is important to confirm that the level of protein expression of the identified genes is also altered. With available antibodies, Western blotting was performed to examine the protein expression of TrkA/NGF, p75$^{NTR}$, and HAP1. Their expression levels were compared with that of tubulin. Consistent with the RT-PCR and Northern blot analyses, Western blotting showed that the expression of TrkA/NGF, p75$^{NTR}$, and HAP1 is decreased in 150Q cells in comparison with that in wild-type and 20Q control cells. It appears that HAP1's expression is mostly altered in 150Q cells. Western blot examination of two other 150Q cell lines, 150Q-1 and 150Q-5, also revealed decreased HAP1 expression, although the extent of the decrease in expression appeared to be less than that for 150Q-9 cells.

Discussion

Intranuclear mutant huntingtin may interfere with gene expression in PC12 cells by its abnormal interactions with other nuclear molecules, thus leading to multiple cellular defects. Because glutamine carries polar side chains, it has been proposed that the polyglutamine domain forms polar zippers (Perutz et al. (1994) *Proc. Natl. Acad. Sci. USA* 91:5355–5358. Many transcription factors contain a glutamine-rich domain, and the glutamine-rich domain of the transcription factor Sp1 can enhance its transcriptional activity (Courey et al. (1988) *Cell* 55:887–898; Courey et al. (1989) *Cell* 59:827–836; Gerber et al. (1994) *Science* 263:808–811). Thus it is also possible that the expanded polyglutamine in huntingtin affects gene transcription by competing with the glutamine-rich domains of other transcription factors for their regulation of transcriptional activities. Alternatively, expanded polyglutamine-containing huntingtin may abnormally interact with other nuclear proteins. This possibility has been suggested by the findings that SCA1 protein binds to a nuclear protein LANP (Matilla et al. (1997) *Nature* 389:974–978; Skinner et al. (1997) *Nature* 389:971–974).

The present study shows that the expression of a number of transcripts is altered in 150Q cells. With RT-PCR, Northern blotting, and Western blotting, the altered expression of several known genes has been confirmed. The altered expression of these known genes is consistent with cellular defects of 150Q cells. For instance, the NGF receptor mediates neurotrophin-induced neurite outgrowth. The role of HAP1 is thought to be involved in intracellular organelle transport (Gutekunst et al. (1998) *J. Neurosci.* 18:7674–7686; Li et al. (1998) *J. Neurosci.* 18:1261–1269; Martin et al. (1999) *J. Comp. Neurol.* 403:421–430, which is also important for neurite development. Decreased expression in NGF receptors and HAP1 could contribute to defective neurite outgrowth. Staurosporine may partially alter or correct abnormal gene expression such that it induces neurite outgrowth of 150Q cells. Because metallothionein can protect cells from oxidative damage (Karin (1985) *Cell* 41:9–10; Schwarz et al. (1995) *Proc. Natl. Acad. Sci. USA* 92:4452–4456) and glutamate mediates excitotoxicity, the decreased expression of metallothionein and the increased expression of the glutamate transporter may also be associated with cell death in 150Q cells. The idea that intranuclear mutant huntingtin affects gene expression is also suggested by a recent study showing that HD transgenic mice have altered transcript expression of multiple neurotransmitter receptors (Cha et al. (1998) *Proc. Natl. Acad. Sci. USA* 95:6480–6485. The present study substantiates this idea and additionally suggests that intranuclear huntingtin can affect gene transcription and cellular defects in the absence of aggregates.

Example 4

Production of a Mouse Monoclonal Antibody to Human Huntingtin Protein

A monoclonal antibody specific to N-terminal fragments of huntingtin which reacts strongly with mutant huntingtin but weakly with wild-type rodent huntingtin was generated. The antigen (an immunogenic polypeptide) was generated by RT-PCR to obtain a truncated human CDNA encoding the first 256 amino acids of human huntingtin with an in-frame deletion of the polyglutamine stretch. The sense oligonucleotide primer used was 5'-TCGAGGTCGACCATG-GCTACGTTAGAGAAATTAATGAAGGCTTTTGAGA-GTTTAAAAAGTTTTCAACAGCCGCCA (SEQ ID NO: 14) and the antisense primer used was 5'-GAAGGCCTTTAACAAAACCTTAATTTC (SEQ ID NO:15). The resulting huntingtin CDNA had two CAG's (glutamines) and an in-frame deletion of the polyproline stretches. This CDNA was inserted into the pGEX vector (Pharmacia) to generate a fusion protein. The GST fusion protein was purified from bacteria and used as an immunogen (antigen). The amino acid sequence of the immunogenic polypeptide encoded by this CDNA is provided in SEQ ID NO:1.

Four 10 week old female BALB/c mice were each immunized subcutaneously and intraperitoneally with 0.2 ml of an emulsion containing equal volumes of immunogen and Freund's complete adjuvant (Sigma Chemical Co., St. Louis, Mo.). The mice were boosted twice by subcutaneous and intraperitoneal injections with the same dose of antigen emulsified in incomplete Freund's adjuvant (Sigma) at four week intervals. Sera were collected, eight days after boosting, by tail vein bleeding and tested for specific antibody production by enzyme-linked immunosorbent assay (ELISA). Four days prior to the fusion, the mouse showing the highest titer was injected intraperitoneally with 25 μg of immunogen in 0.01 M phosphate-buffered saline (PBS), pH 7.2.

Two days prior to fusion, mouse peritoneal feeder cells were collected from a normal, unimmunized BALB/c mouse that had been primed with pristane (2,6,10,14-tetramethylpentadecane, Sigma Chemical Co., St. Louis, Mo.) for two weeks. Feeder cells were seeded in 96-well plates at a concentration of 10$^4$ cells per well in RPMI 1640 (Sigma) medium supplemented with 15% fetal bovine serum, 2 mM-glutamine, and antibiotics (100 U penicillin ml$^{-1}$, and 100 μg streptomycin ml$^{-1}$). The immunized mouse with the highest titer was sacrificed by cervical dislocation for hybridoma production. The spleen was removed aseptically and splenocytes were harvested and washed twice in serum-free RPMI 1640 medium. Mouse myeloma cells (P3X63.Ag8.653; ATCC CRL 1580) were harvested from exponentially growing cultures and also washed twice in serum-free RPMI 1640. Splenocytes and myeloma cells were counted and combined at a ratio of 2 splenocytes to 1 myeloma and spun in a 50 ml conical tube at 200×g for 10 min at room temperature. After complete aspiration of the supernatant medium, 1 ml of 50% polyethylene glycol 4000 (PEG; Sigma) was added dropwise to the pellet with gentle mixing for 90 sec and the PEG was slowly diluted (initially dropwise) with serum-free medium over a period of 7 min. After centrifugation at 25×g, the supernatant was aspirated and the cell pellet was resuspended in complete growth medium supplemented with hypoxanthine $10^{-4}$ M, aminopterin $4×10^{-7}$ M, and thymidine $1.6×10^{-5}$ M (HAT medium). Fused cells were distributed into eight, 96-well tissue culture plates (150 μl per well) and incubated at 37° C. with 5% $CO_2$. Five days post fusion, one-half of the spent culture medium was removed and replaced with HAT medium. Approximately two weeks post fusion, supernatants from wells with growing hybrids which were at least 15% confluent were removed and tested by ELISA for specific antibody. Positive hybridomas were subcloned twice by limiting dilution using a peritoneal feeder cell layer.

An enzyme-linked immunosorbent assay (ELISA) was used for detection of specific antibody. Protein, at a concentration of 0.25 μg per well in 100 μl of carbonate buffer (0.06 M, pH 9.6), was coated to each well of 96-well microtiter plates (polyvinyl chloride plates, Costar) and incubated for 1 hr at 37° C. or at 4° C. overnight. After the plates were washed three times with PBST (0.1 M phosphate-buffered saline containing 0.5% Tween-20), 100 μl of 1% bovine serum albumin (BSA) in PBS was added to each well to block nonspecific binding sites and the plate was incubated for 1 hr at 37° C. After the plates were washed three times with PBST, 100 μl of hybridoma cell supernatant was added to each well and incubated for 1 hr at 37° C. After another three washes with PBST, 100 μl of diluted (1:3,000 in PBS) horseradish peroxidase-conjugated goat anti-mouse IgG (Fc specific) (Sigma) was added. Following 1 hr incubation at room temperature, the plate was washed four times with PBST, and 100 μl of substrate solution containing o-phenylenediamine (OPD; Sigma) and hydrogen peroxide (Sigma). After a 10 min incubation at room temperature, the reaction was stopped by adding 50 μl of 8 N $H_2SO_4$ and the absorbance was measured at 490 nm with an automated microplate reader (Perkin-Elmer Lambda Reader).

Example 5
Use of a Mouse Monoclonal Antibody to Human Huntingtin to Demonstrate that Intranuclear Huntingtin Protein Interferes with HAP1-A Promoted Neurite Outgrowth It has been demonstrated that polyglutamine expansion can enhance the interaction between huntingtin protein and HAP1-A (Li et al. (1995) Nature 378:398–402; Li et al. (1998) J. Neurosci. 18:1261–1269). The present study was designed to examine the effect of expanded polyglutamine-containing huntingtin protein on HAP1-A promoted neurite outgrowth.

Material and Methods

RT-PCR. HAP1-A and HAP1-B cDNAs are derived from the same gene by alternative splicing, which results in different nucleotide sequences in the coding regions of their C-termini (Li et al. (1995) Nature 378:398–402). CDNA sequences specific for HAP1-A and HAP1-B isoforms were used to design oligonucleotide primers for detecting their expression by RT-PCR. Five micrograms of total RNA, prepared from a variety of rat tissues and PC12 cells, was reverse transcribed to CDNA in a 20-μl reaction mixture. Synthesized cDNA (1 μl) and the respective primers were added to a 50-μl reaction mixture containing 20 mM Tris-HCl (pH 8.4), 50 mM KCl, 2.5 mM $MgC_{12}$, all four dNTPs (each at 250 μM), 1 unit of Taq polymerase (Boehringer Mannheim, Indianapolis, Ind.), and 0.2 μM primers. Twenty-five or thirty cycles were carried out for HAP1-B or HAP1-A PCR in a thermal cycler (Perkin-Elmer 480); each cycle consisted of incubation at 95° C. for 1 min, 60° C. for 1 min, and 72° C. for 2 min. The PCR products were separated on a 1.0% agarose gel. Controls were RT-PCRs without reverse transcriptase ($dH_2O$) or with cloned HAP1-A or HAP1-B cDNA (10 ng).

Antibodies and Western blots. The mouse anti-huntingtin monoclonal antibody is described supra.

Cell cultures. Rat adrenal pheochromocytoma PC12 cells were provided by Dr. James J. Lah (Department of Neurology, Emory University; Lah and Burry, 1993). PC12 cells were grown in DMEM supplemented with 10% horse serum and 5% fetal bovine serum and incubated at 37 C. in a humidified 5% CO, atmosphere. Cells were plated onto chamber slides at densities ranging from 5000 to 10,000 cells/$cm^2$. When appropriate, 100 ng/ml NGF (2.5 S; Life Technologies, Gaithersburg, Md.) was incubated with the PC12 cells for 48 h to induce neurite outgrowth.

Immunofluorescence. Cultured cells were fixed in 4% parafornaldehyde in PBS for 15 min at room temperature. The cells were then blocked and permeabilized in a solution of 3% BSA and 0.2% Triton X-100 in PBS for 1 h at room temperature. After fixation, the cells were rinsed with PBS and then permeabilized by incubation with 0.1% Triton X-100 in PBS for 10 min. The cells were blocked in 3% BSA in PBS. Primary antibodies were incubated with the cells at 4° C. overnight in the blocking solution. After three washes with PBS, goat anti-mouse or anti-rabbit IgG conjugated to fluorescein or rhodamine (Jackson ImmunoResearch Laboratories, West Grove, Pa.) was added to blocking solution and applied to the cells for 60 min at room temperature. Cells were mounted in Vectashield mounting medium (Vector Laboratories, Inc., Burlingame, Calif.) to resist bleaching. Neurons were viewed on a Zeiss Axioskop (Carl Zeiss, Inc., Thornwood, N.Y.) with a 3CCD camera video system (Dage-MTI, Michigan City, Ind.). The captured images were stored and processed using Adobe PhotoShop 5.0 soft-ware. All backgrounds were adjusted to equality to ensure that the images could be legitimately compared.

cDNA constructs and transfection of cells. Cloned HAP1-A and HAP1-B cDNAs were inserted into the expression vector pCIS (Li et al., 1995) carrying the cytomegalovirus promoter. The expression constructs encoding N-terminal human huntingtin (253 amino acids) with 23, 73, or 120 glutamines were obtained in a previous study (Li and Li, 1998). PC12 cells were plated onto two-well chamber slides at a density of 50,000/$cm^2$ and cultured for 24 h. Two micrograms of plasmid DNA was then added to each well in a 1-ml solution containing Lipofectamine (10 μg/ml), yielding 3–8% transfected cells. Following 18–24 h transfection, the media were replaced with fresh growth media and the cells were grown for another 24 h before immunofluorescent staining. The immunostaining images were captured using a 3CCD camera video system. Neurite length was measured as cell body diameters. The average sizes (μm) of perinuclear huntingtin inclusions were obtained by measuring the diameters of inclusions in 58–112 cells transfected with huntingtin alone. The percentage of transfected cells with neurites that exceeded two body diameters was obtained by counting 200–300 transfected cells in three independent experiments. For double transfection, equal amounts (2 μg for each) of HAP1-A and huntingtin cDNAs were transfected into PC12 cells in each well of six-well dishes. The transfected cells were immunostained with the rabbit polyclonal antibody for HAP1-A and mouse monoclonal antibody for huntingtin.

Results

Because overexpressed HAP1-A promotes neurite outgrowth, both HAP1-A and human huntingtin were cotransfected into PC12 cells to assess the specific effect of huntingtin on the overexpressed HAP1-A. To confirm that the observed effects were associated with polyglutamine length, three human huntingtin constructs encoding the N-terminal region of huntingtin protein (amino acids 1–253) with 23 (HD-23Q), 73 (HD-73Q), or 120 (HD-120Q) glutamines were used. Transfection of HAP1-A alone promoted neurite outgrowth and resulted in small cytoplasmic puncta. No strong staining of endogenous rodent huntingtin was seen to associate with these puncta, perhaps because of a weak immunoreaction of the anti-huntingtin antibody with rodent huntingtin or the weak binding of HAP1 to rodent huntingtin, which has only seven glutamine repeats. Transfection of HD-120Q alone, however, produced perinuclear inclusions that are highly huntingtin immunoreactive and significantly larger than HAP1-A puncta. Cotransfection of human huntingtin (HD-23Q) with HAP1-A into PC12 cells resulted in a diffuse distribution of HD-23Q and punctate staining of HAP1-A. Diffuse cytoplasmic labeling of HAP1-A in these double-transfected cells was also evident, suggesting that some HAP1-A is associated with diffuse HD-23Q. The HD-23Q, HAP1-A double-transfected PC12 cells showed spontaneous neurite out-growth. When PC12 cells were transfected with HAP1-A and HD-73Q, they displayed large perinuclear aggregates that were labeled by both anti-huntingtin and anti-HAP1 antibodies. This result suggests that both HAP1-A and HD-73Q are associated in the aggregates. Some HAP1-A was also localized in neurites, as small puncta in the processes were labeled only by anti-HAP1-A antibody. PC12 cells were also transfected with HD-120Q. In this case, much larger huntingtin aggregates were present in the perinuclear region. These large aggregates were also strongly immunoreactive to the antibody against HAP1-A, suggesting that most of the transfected HAP1-A is localized in the aggregates. Inmost PC12 cells that had large cytoplasmic aggregates, there were no obvious neurites or, if short neurites were present, they contained very few small HAP1-A-immunoreactive puncta.

It was also observed that larger huntingtin inclusions contain more HAP1-A staining. Since HAP1-A binds more tightly to huntingtin containing an expanded polyglutamine (Li et al. (1995) *Nature* 378:398–402), it was examined whether transfected huntingtin containing a longer glutamine repeat forms larger perinuclear inclusions. By measuring the diameters of a number of perinuclear inclusions, it was observed that HD-120Q formed larger perinuclear inclusions than HD-73Q and HD-23Q.

A quantitative assessment of the number of transfected cells containing neurites and the length of these neurites was also performed. In HAP1-A transfected PC12 cells, 29.4% had significant spontaneous neurites, whereas 4.7% of cells transfected with vector alone had neurites. In contrast, only 9.7% of HAP1-B-transfected cells displayed such neurites. Similarly, very few huntingtin-transfected cells showed neurites (5.1% for HD-20Q-, 4.5% for HD-72Q-, and 3.8% for HD-120Q-transfected cells). The length of the neurites in HAP1-A-transfected cells (3.8 body diameters) was also longer than that of HAP1-B-transfected cells (1.9 body diameters). In HAP1-A and huntingtin double-transfected PC12 cells, 24.6, 15.2, and 7.5% of cells expressing HD-23Q, HD-73Q, and HD-120Q, respectively, had elongated neurites. Compared to the cells transfected with HAP1-A alone, it was concluded that truncated mutant huntingtin can inhibit the neurite outgrowth promoted by HAP1-A. Since HAP1-A is localized to huntingtin aggregates, it is likely that huntingtin inclusions recruit transfected HAP1-A, and thus inhibit its effect on neurite outgrowth.

Discussion

Given that HAP1-A is important for neuritic out-growth and synaptic function and that HAP1-A binds more tightly to mutant than wild-type huntingtin, it is reasonable to propose that the abnormal interaction of mutant huntingtin and HAP1-A may contribute to neuritic pathology. Current evidence, however, suggests that mutant huntingtin acts in presynaptic terminals to affect synaptic function. For instance, transgenic mutant huntingtin impairs long-tern potentiation in hippocampal slices from mice at the age of 8–14 months (Hodgson et al. (1999) *Neuron* 23:181–192; Usdin et al. (1999) *Hum. Mol. Genet.* 8:839–346). Consistent with this hypothesis, huntingtin aggregates are found in axonal terminals, and the formation of neuropil aggregates is correlated with the progression of neurological symptoms in HD transgenic mice (Li et al. (1999) *Hum. Molec. Genet.* 8:1227–1236).

Although a previous study using an antibody against both HAP1-A and HAP1-B did not reveal HAP1 immunostaining of large intranuclear aggregates in HD patients' brains (Gutekunst et al. (1998) *J. Neurosci.* 18:7674–7686), mutant huntingtin or its small aggregates could bind to HAP1-A in neurites and axon terminals. The colocalization. of both mutant huntingtin and transfected HAP1-A in PC12 cells suggests that huntingtin aggregates recruit HAP1-A. The inhibitory effect of huntingtin aggregates on HAP1-A promoted neurite outgrowth raises the possibility that huntingtin aggregates could also affect the functioning of HAP1-A in neuronal processes in HD brains. If so, the resulting neuronal dysfunction is likely to occur in adult neurons, as the formation of neuropil aggregates occurs in mature neurons and requires the proteolytic processing of full-length mutant huntingtin.

That which is claimed:

1. A hybridoma cell line that produces a monoclonal antibody that preferentially binds to the polypeptide of SEQ ID NO:1; wherein said monoclonal antibody has the binding characteristics of the monoclonal antibody produced by the hybridoma cell line deposited with ATCC as Patent Deposit Number PTA-2179.

2. The hybridoma cell line deposited with ATCC as Patent Deposit No. PTA-2179.

3. The monoclonal antibody produced by the hybridoma cell line deposited with ATCC as Patent Deposit Number PTA-2179.

4. A monoclonal antibody having the binding characteristics of the monoclonal antibody produced by the hybridoma cell line deposited with ATCC as Patent Deposit Number PTA-2179.

* * * * *

UNITED STATES PATENT AND TRADEMARK OFFICE
CERTIFICATE OF CORRECTION

PATENT NO. : 6,355,481 B1
DATED : March 12, 2002
INVENTOR(S) : Li et al.

It is certified that error appears in the above-identified patent and that said Letters Patent is hereby corrected as shown below:

Column 1,
Line 11, insert the following paragraph before "FIELD OF THE INVENTION":
-- FEDERALLY SPONSORED RESEARCH OR DEVELOPMENT
The research underlying this invention was supported in part with funds from National Institute of Health Grant No. CA7733. The United States Government may have an interest in the subject matter of this invention. --.

Signed and Sealed this

Sixth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,355,481 B1
DATED : March 12, 2002
INVENTOR(S) : Li et al.

It is certified that error appears in the above-identified patent and that said Letters Patent is hereby corrected as shown below:

Column 1,
Line 11, insert the following paragraph before "FIELD OF THE INVENTION":
-- FEDERALLY SPONSORED RESEARCH OR DEVELOPMENT
This invention was made with government support under Grant No. CA077337 awarded by the National Institutes of Health. The government has certain rights in the invention. --.

Signed and Sealed this

Tenth Day of January, 2006

JON W. DUDAS
*Director of the United States Patent and Trademark Office*

SEQUENCE LISTING

<160> NUMBER OF SEQ ID NOS: 15

<210> SEQ ID NO 1
<211> LENGTH: 34

```
<212> TYPE: PRT
<213> ORGANISM: Homo sapiens

<400> SEQUENCE: 1

Met Ala Thr Leu Glu Lys Leu Met Leu Ala Phe Glu Ser Leu Lys Ser
1               5                   10                  15

Phe Gln Gln Pro Pro Pro Pro Gly Pro Ala Val Ala Glu Glu Pro Leu
            20                  25                  30

His Arg

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
acgacccctt cattgacctc                                             20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
gggggctaag cagttggtgg                                             20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tgtggaagtg ggggatgacg                                             20

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
gcactcagca agaaagacct                                             20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ccacattccg acgactgatg                                             20

<210> SEQ ID NO 7
<211> LENGTH: 20
<212> TYPE: DNA
```

<213> ORGANISM: Artificial Sequence
<220> FEATURE:
<223> OTHER INFORMATION: PCR primer

<400> SEQUENCE: 7
ccaagaatga gcgcactaac                                          20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
ggagagcagg acggactttt                                          20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9 ccagagggt catcaatcca                                           20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
ggttttcatt ggagggttgc                                          20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
ctgtctgcca cgggtttctc                                          20

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
cagcgttgta cgtcttatgg g                                        21

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
ggggattggt ccaactgtgg                                          20

```
<210> SEQ ID NO 14
<211> LENGTH: 75
<212> TYPE: DNA
<213> ORGANISM: Artificial Sequence
<220> FEATURE:
<223> OTHER INFORMATION: PCR primer

<400> SEQUENCE: 14
tcgaggtcga ccatggctac gttagagaaa ttaatgaagg cttttgagag tttaaaaagt      60
tttcaacagc cgcca                                                       75

<210> SEQ ID NO 15
<211> LENGTH: 27
<212> TYPE: DNA
<213> ORGANISM: Artificial Sequence
<220> FEATURE:
<223> OTHER INFORMATION: PCR primer

<400> SEQUENCE: 15
gaaggccttt aacaaaacct taatttc                                          27
```